United States Patent [19]
Stavropoulos et al.

[11] 3,938,954
[45] Feb. 17, 1976

[54] DETERMINATION OF CALCIUM
[75] Inventors: William S. Stavropoulos, Carmel; Bernard J. Thiegs; Robert F. Mack, both of Indianapolis, all of Ind.
[73] Assignee: The Dow Chemical Company, Midland, Mich.
[22] Filed: Jan. 20, 1975
[21] Appl. No.: 542,528

Related U.S. Application Data
[63] Continuation of Ser. No. 350,278, April 11, 1973, abandoned.

[52] U.S. Cl. ............................ 23/230 B; 252/408 R
[51] Int. Cl.$^2$ .......................................... G01N 33/16
[58] Field of Search ...... 23/230 B, 253 TP; 252/408

[56] References Cited
OTHER PUBLICATIONS
Zak et al., *Adv. in Automated Analysis*, 1972 Technicon International Congress, Mediad Inc., Vol. 1 pp. 151–157 (1972).
Connerty et al., *Am. J. Clin. Path.*, Vol. 45, pp. 290–294 (1966).
Moorehead et al., *Clin. Chem.*, Vol. 20, pp. 1458–1460 (1974).

*Primary Examiner*—Joseph Scovronek
*Assistant Examiner*—Timothy W. Hagan
*Attorney, Agent, or Firm*—Maynard R. Johnson

[57] ABSTRACT

An improved reagent system for determining calcium by the orthocresolphthalein complexone color reaction. The reagent utilizes an alkaline buffer containing an aminoloweralkanol providing a pH of about 10.2 – 10.5. A method for using the reagent is also described. The composition is stable for extended periods.

8 Claims, No Drawings

DETERMINATION OF CALCIUM

This is a continuation of application Ser. No. 350,278 filed Apr. 11, 1973, now abandoned.

BACKGROUND OF THE INVENTION

The determination of calcium in biological fluids using an orthocresolphthalein complexone reagent composition is an accepted method in many hospital, industrial, reference and commercial clinical laboratories. The method is based on the use of the acid-base indicator orthocresolphthalein complexone, also named as 3',3''-bis([bis(caboxymethyl)-amino]-methyl)-5',5''-dimethylphenolphthalein and abbreviated as "OCPC", to form a measurable color with calcium under alkaline conditions. A neutral or acid solution of the compound is colorless; alkaline solutions are violet, the intensity of the color deepening as the pH increases.

The method is usually carried out by mixing a color reagent, contaning orthocresolphthalein complexone in a dilute hydrochloric acid solution, and an alkaline reagent, containing an amine base and a small amount of an alkali metal cyanide, with a biological fluid. The acid and the amine base provide an alkaline buffer which gives a suitable pH, usually pH 11, in the ultimate mixture. The intensity of the resulting color is measured photometrically after a predetermined time interval at a predetermined temperature. orthocresolphthalein complexone methods for determination of calcium have been described, for example, by Stern et al., Clin. Chem. 2, 576 (1957); Gitelman, Analytical Biochemistry, 18, 521 (1967) and Connerty et al., Am. J. Clin. Path. 45, 290 (1966). The determination may be carried out in the presence of a small amount of 8-quinolinol, to minimize interference by magnesium ion, as taught by Connerty et al., supra. Potassium cyanide has also been employed in such methods to minimize interference by heavy metals.

Diethylamine is generally employed as the amine base. Diethylamine has an offensive odor and a low flash point, and diethylamine reagents are unduly sensitive to both pH and calcium concentration. It would be desirable to eliminate its use in calcium determinations. Connerty and Briggs, supra, described a reagent in which a 0.74 molar, pH 11 aminoethanol borate buffer (AEB) is employed. The AEB system required protein precipitation or calcium oxalate precipitation before analysis, and is thus unsuitable for direct analyses on small serum samples. Also, the AEB reagent is oversensitive to calcium, giving absorbance values of 0.5 and higher for calcium levels near the high end of the normal range, making the results difficult to read accurately.

BRIEF SUMMARY OF THE INVENTION

This invention relates to an improvement in orthocresolphthalein complexone reagent compositions used for determination of calcium concentration in biological fluids such as blood serum, plasma, urine, etc. The invention provides a reagent composition wherein the amine base in the alkaline buffer is an aminoloweralkanol and a direct method for using the same to determine the concentration of calcium in biological fluids.

The invention is further characterized in that the acid and amine base are employed in the alkaline buffer in proportions which provide a pH of from about 10.1 to about 10.7 in the reagent composition.

The amine base is an aminoloweralkanol of three or four carbon atoms, and having a dissociation constant, pK, in water of from about 9.3 to about 10. The aminoalkanol can be a primary amine such as 3-amino-1-propanol, provided it has the proper pK. A preferred amine base is 2-ethylaminoethanol. Amines having a pK substantially above or below the above-stated range, such as diethylamine (pK 10.9) or 2-dimethylaminoethanol (pK 9.2) provide reagent compositions which are undesirably sensitive to minor changes in amine concentration, and which also can be undesirably oversensitive or undersensitive to calcium concentration.

The reagent composition and method of the invention thus eliminate the use of diethylamine, and with it the problem of its offensive odor, and the hazard associated with the low flash point of diethylamine. Additionally, the invention provides a reagent and method of reduced sensitivity to minor differences in pH, such as may result from pipetting errors in formulating the reagent. Further, the invention provides improved sensitivity to calcium concentration over the range normally encountered in determinations on human serum.

In preparing the reagent composition of the invention, the orthocresolphthalein complexone, a suitable acid, the amine base and optionally sodium or potassium cyanide, 8-hydroxyquinoline, and a water-soluble surfactant such as a ethoxylated fatty alcohol or a polysorbate, are dissolved in water in similar proportions and in a similar manner to that employed in preparing known orthocresolphthalein complexone reagents, with the exceptions that the amine base is an aminoloweralkanol and the pH of the ultimate reagent is within the above-stated range. In a convenient embodiment the reagent composition is prepared by separately preparing an acidic color reagent, containing the orthocresolphthalein complexone and the acid, and an alkaline reagent, containing the aminolowerakanol. The acidic color reagent and the alkaline reagent are mixed together to provide the ultimate composition having the required pH.

In the acidic color reagent the orthocresolphthalein complexone and ingredient is generally employed in amounts of from about 0.01 to about 0.03 to about 0.07 to about 0.1 gram per liter and 8-quinolinol is employed at a concentration of from zero to about 5 grams per liter; a surfactant (such as the polyoxyethylene laurylethers sold under the name Brij) is employed at a concentration of about 0.5 to about 5 grams per liter and an acid which is compatible with the other ingredients and which does not interfere with the color reaction is employed in an amount sufficient to provide an acid normality of from about 0.1 to about 0.5 normal. The alkaline reagent is prepared separately to contain from about 30 to about 150 grams of aminoloweralkanol per liter and can also contain from about zero to about one gram of alkali metal cyanide per liter. The two aqueous reagents can be stored in bulk or dispensed into vials or curvets for storage in unitized kit form prior to use. In use, the color reagent and alkaline reagent are mixed in such proportions as will provide an alkaline pH of from about 10.1 to about 10.7 in the ultimate mixture with the biological fluid.

The exact relative proportions of the orthocresolphthalein complexone, the acid, the aminoloweralkanol, and the surfactant and other ingredients (if employed) in the ultimate reagent composition, as well as the parameters of the analytical procedure such as relative proportions of color reagent, alkaline reagent and standard or sample, pH, amount wavelength of light at which color intensity is measured, etc., are determined in accordance with known procedures. A preferred color reagent composition contains about 0.025 to 0.1 gram of orthocresolphthalein complexone, from about one to about 5 grams of 8-quinolinol, and about 0.5 to 2.5 gram of surfactant per liter of aqueous hydrochloric acid, about 0.2 to 0.3 normal. A preferred alkaline reagent contains from about 40 to about 120 grams of aminoloweralkanol and from about 0.05 to about 0.25 gram of potassium cyanide per liter of water. The two compositions are mixed in approximately equal proportions to provide the ultimate reagent composition of the invention.

A preferred ultimate composition contains from about 0.012 to about 0.5 gram of orthocresolphthalein complexone, from about 20 to about 60 grams aminoloweralkanol per liter, in aqueous hydrochloric acid, from about 0.1 to about 0.2 normal. The preferred ultimate composition will also contain about 0.05 – 2.5 grams 8-quinolinol and 0.025 – 0.125 grams potassium cyanide per liter. This composition is preferably employed in calcium determination by mixing one part by volume of a biological fluid sample, a standard solution or control serum with about 50 to 300 parts by volume of ultimate reagent composition and holding the mixture for a time sufficient for development of a conveniently measurable color. Excellent results can be obtained in 2–10 minutes at ambient temperatue.

The resulting red color is then measured in a spectrophotometer or colorimeter, or compared to visual standards, or the like to provide a measurement of calcium concentration. The color intensity is preferably measured in a spectrophotometer or colorimeter with light having a wavelength of 540 to 580 millimicrons (nanometers).

DESCRIPTION OF PREFERRED EMBODIMENTS

The following examples are illustrataive and representative of the invention.

EXAMPLE 1

A calcium reagent composition is prepared by mixing together the following ingredients in the following proportions:

| Acidic Color Reagent | orthocresolphthalein complexone in 0.25 N hydrochloric acid. |
|---|---|
| o-Cresolphthalein complexone | 50 mg |
| Hydrochloric acid (37 percent in water) | 21.0 ml. |
| 8-Hydroxyquinoline | 2.5 grams |
| Aqueous 30 percent - Surfactant Solution (Brij-35) | 1.0 ml. |
| Distilled water | q.s. to 1 liter |
| Alkaline Reagent | |
| 2-Ethylaminoethanol | 60.0 grams |
| Potassium Cyanide | 0.125 gram |
| Distilled Water | q.s. to 1 liter |

2 Milliliters of each composition are transferred to each of a series of ten vials and mixed well. Seven vials are employed for determination of calcium in a control serum having a stated calcium concentration of 4.5 – 4.9 milliequivalents (mEq) of calcium per liter. Two vials are used as standards with a standard solution of calcium carbonate in aqueous 0.01 N hydrochloric acid, containing 5 mEq calcium per liter. 50 Microliters of the appropriate fluid (control serum or standard solution) are added to each vial and the contents are mixed. 50 Microliters of distilled water are mixed with the contents of one vial to serve as a blank. After 5 minutes color development at room temperature (about 25°C.) the intensity of the red color in each vial is then measured by measuring absorbance at 565 nanometers usng a photoelectric colorimeter. (The instrument is previously adjusted to zero absorbance using distilled water). The calcium of the control serum sample is calculated for each vial by dividing the difference between the absorbance measured with a control serum vial (sample) and the blank vial by the difference between the average absorbance measured with the two standard solution vials and the blank vial, and multiplying the quotient by a factor. (The factor is determined by the calcium content of the standard solution used. In this case, the factor is 5 and the result obtained is expressed in milliequivalents of calcium per liter of serum.)

In these operations, the absorbance times 100 (A × 100) measured with the blank is 12.7, the average A × 100 with the standard solution is 46.75 and the calcium concentration results obtained with each of the seven control serum determinations are 4.6, 4.6, 4.7, 4.6, 4.6, 4.7 and 4.6.

EXAMPLE 2

In a procedure similar to that described in Example 1 two series of reagent compositions are prepared. In the first series, the alkaine reagent employed is similar to that of Example 1, except that diethylamine (having a pK of about 10.9) is employed as the amine base. In the second series, the amine base 2-ethylaminoethanol (having a pK of about 9.9) is employed in various concentrations. The pH of the reagent compositions is measured and the compositions are then mixed with 50 microliters of a calcium standard solution of b 1 or with distilled water (blank) and absorbance is determined as described in Example 1.

The results indicate that the compositions containing diethylamine as the amine base are extremely sensitive to amine base concentration. The compositions prepared from alkaline reagents containing from 3.0 to 5.0 milliliters of diethylamine per 100 milliliters (3.0 to 5.0% v/v) have pH's ranging from about 9.82 – 9.92 at the 3 percent level to 11.03 – 11.04 at the 5 percent level. Blank absorbance is also found to increase undesirably with the concentration of amine base, from A × 100 of about 8.4 – 8.8 at the 3.0 percent level to 11.1 – 11.6 at the 3.25 percent level, 13.8 at the 3.75 percent level, up to an undesirable high blank of 19.3 – 20.0 at the 5.0 percent level. The standard absorbance and corrected absorbance (standard minus blank) also increases markedly with minor increases in diethylamine concentration. Standard absorbance (A × 100) increases from 27.0 – 29.1 to 76.0 and corrected absorbance increases from 1.6 – 20.3 to 56.0 – 56.7 as the diethylamine level increases from 3.0 to 5.0 percent.

In contrast, the reagent compositions prepared with alkaline reagents containing from 5.0 to 10.0 grams of 2-ethylaminoethanol per 100 milliliters (5.0 to 10.0 percent w/v) are found to be much less sensitive to changes in amine level. The pH at the 5.0 percent level is 10.17 – 10.18, increasing to 10.62 – 10.63 at the 10.0 percent level. Blank, standard and corrected absorbance times 100 at the 5.0 percent amine level are 10.0 – 10.2, 38.9 – 39.0 and 28.8 – 28.9, respectively. With the compositions containing 10.0 percent (w/v) of 2-ethylaminoethanol, the corresponding results are 11.5 – 12.0, 52.2 – 52.5 and 40.5 – 40.7.

In a similar operation, alkaline reagents contaning either diethylamine in a concentration of 32.5 ml. per liter or 2-ethylaminoethanol in a concentration of sixty grams per liter are prepared. The alkaline reagent compositions are employed with a color reagent composition of Example 1 to determine variations in blank absorbance which could result from pipetting errors. 50 Microliters of distilled water are employed as a blank, and two milliliters of color reagent are employed. Various amounts of alkaline reagent in increments of 0.1 millilter are employed to stimulate pipetting errors. The average blank absorbance × 100 obtained with each reagent are set out below:

| Milliliters of | Absorbance × 100 | |
| Alkaline Reagent | Diethylamine | 2-Ethylaminoethanol |
| --- | --- | --- |
| 1.8 | 7.65 | 11.25 |
| 1.9 | 9.55 | 11.05 |
| 2.0 | 10.8 | 11.15 |
| 2.1 | 11.7 | 10.95 |
| 2.2 | 10.05 | 10.9 |

The above results indicate that minor pipetting errors can substantially alter results obtained with the diethylamine reagent, whereas the 2-ethylaminoethanol reagent is relatively insensitive to such minor errors.

EXAMPLE 3

In a smilar procedure, a series of reagent compositions are prepared using different amounts of different amine bases in the alkaline reagent. Two milliliters of each alkaline reagent are mixed with 2 milliliters of an orthocresolphthalein complexone reagent to prepare a series of calcium reagent compositions (prepared as described above in Example 1). The final reagents are then mixed with 50 microliters of distilled water or a calcium standard solution containing 5 mEq calcium per liter and color is developed and measured as described above. The amine bases employed, the concentration of the base in the alkaline reagent (in grams per liter), the pH of the resulting composition and the blank and corrected standard absorbance values are set out below:

| Amine in Alkaline Reagent | pK of Amine | Concentration (grams/liter) | pH | Absorbance × 100 | |
| | | | | Blank | Corrected Standard |
| --- | --- | --- | --- | --- | --- |
| 2-Ethylaminoethanol | 9.9 | 60.0 | 10.36 | 11.3 | 33.2 |
| 2-Methylaminoethanol | 9.6 | 60.0 | 10.37 | 12.4 | 35.1 |
| 3-Amino-1-propanol | 9.4 | 40.0 | 10.32 | 13.9 | 33.3 |
| 2-Aminoethanol | 9.4 | 100 | 10.44 | 12.9 | 35.1 |
| 2-Amino-2-methyl-1-propanol | 9.3 | 100 | 10.42 | 11.7 | 32.3 |
| 2-Dimethylaminoethanol | 9.2 | 150 | 10.24 | 7.3 | 20.7 |

In other operations, the reagent composition and method of Example 1 is evaluated in a standard sequence of tests for analysis of calcium in human serum. The reagent and method are found to give linear results with calcium concentrations of up to 10 mEq per liter (normal adult levels are from about 4.6 to 5.6 mEq per liter). The reagent and method are free of interference by bilirubin up to 20 mg per 100 ml, phosphate up to at least 40 mg per 100 ml, magnesium up to levels of ten times normal magnesium levels, and hemoglobin (in hemolyzed serum) of up to 150 mg per 100 ml.

It will be apparent to those skilled in the art that numerous variations can be made in the use of the invention, for example, by varying the concentration of the orthocresolphthalein complexone and by varying the amounts and the nature of other ingredients in adapting the reagent and method to particular analytical systems, or in the order of mixing the ingredients and samples while utilizing the invention.

What is claimed is:

1. In a reagent composition useful for determination of calcium in biological fluids by measuring the intensity of color produced by orthocresolphthalein complexone in an aqueous alkaline buffer solution, the composition comprising a solution of orthocresolphthalein complexone, in an aqueous alkaline amine base buffer, the improvement wherein the amine base is an aminoloweralkanol of three or four carbon atoms, having a pK of from about 9.3 to about 10, and wherein the reagent composition has a pH of from about 10.1 to about 10.7.

2. The composition of claim 1 wherein the aminoloweralkanol is 2-ethylaminoethanol.

3. The composition of claim 2 wherein the buffer comprises 2-ethylaminoethanol in a concentration of from about 20 to about 60 grams per liter in aqueous hydrochloric acid from about 0.1 to about 0.2 normal.

4. The composition of claim 1 wherein the pH of the composition is from about 10.3 to about 10.5.

5. In a method for determination of calcium comprising the steps of mixing together predetermined quantities of a biological fluid, orthocresolphthalein complexone, as the essential color forming reagent, and an alkaline buffer comprising an amine base, incubating the mixture for a predetermined period under predetermined conditions of temperature, and measuring the intensity of the resulting color, the improvement wherein: the amine base is an aminoloweralkanol of three or four carbon atoms, having a pK of from about 9.3 to about 10, and wherein the ingredients are mixed together in proportions sufficient to provide a pH of from about 10.1 to about 10.7 in the ultimate mixture.

6. The method of claim 5 wherein the biological fluid is human blood serum, and wherein the amine base is 2-ethylaminoethanol.

7. The method of claim 5 wherein the pH of the ultimate mixture is from about 10.1 to about 10.5.

8. The method of claim 5 wherein the mixing is carried out by mixing a minor amount of human blood serum directly with a reagent composition comprising sufficient orthocresolphthalein complexone to form a measurable color with calcium in the serum, in an aqueous buffer solution of 2-ethylaminoethanol in aqueous hydrochloric acid, the reagent composition having an alkaline pH of from about 10.1 to about 10.7; and wherein the incubation is carried out at room temperature for from about 2 to about 10 minutes.

* * * * *

UNITED STATES PATENT AND TRADEMARK OFFICE
CERTIFICATE OF CORRECTION

PATENT NO. : 3,938,954
DATED : February 17, 1976
INVENTOR(S) : William S. Stavropoulos, Bernard J. Thiegs, et al.

It is certified that error appears in the above-identified patent and that said Letters Patent are hereby corrected as shown below:

Insert omitted heading directly below "DETERMINATION OF CALCIUM" as follows: --Cross-Reference to Related Application--;

Column 1, line 13, "caboxymethyl" should read --carboxylmethyl--;

Column 1, line 21, "contaning" should read --containing--;

Column 1, line 29, "orthocresol-" should read --Orthocresol- --;

Column 2, line 28, "such as a" should read --such as an--;

Column 2, line 38, "aminolowerakanol." should read --aminoloweralkanol.--;

Column 2, line 59, "curvets" should read --cuvets--;

Column 3, line 22, "0.05" should read --0.5--;

Column 3, line 30, "temperatue" should read --temperature--;

Column 3, line 40, "illustrataive" should read --illustrative--;

Column 3, line 48, "Acidic Color Reagent" should read --Acidic Color Reagent - --;

UNITED STATES PATENT AND TRADEMARK OFFICE
CERTIFICATE OF CORRECTION

PATENT NO. : 3,938,954
DATED : February 17, 1976
INVENTOR(S) : W. S. Stavropoulos, B. J. Thiegs, et al.

It is certified that error appears in the above-identified patent and that said Letters Patent are hereby corrected as shown below:

Column 4, line 7, "nanometers usng" should read --nanometers using--;

Column 4, line 30, "alkaine" should read --alkaline--;

Column 4, line 37, "b" should read --Example--;

Column 4, line 57, "1.6" should read --18.6--;

Column 5, line 3, "contaning" should read --containing--;

Column 5, line 13, "millilter" should read --milliliter--;

Column 5, line 31, "smilar" should read --similar--;

Signed and Sealed this

Thirty-first Day of August 1976

[SEAL]

Attest:

RUTH C. MASON
*Attesting Officer*

C. MARSHALL DANN
*Commissioner of Patents and Trademarks*